(12) United States Patent
Hunsley et al.

(10) Patent No.: US 7,767,460 B2
(45) Date of Patent: Aug. 3, 2010

(54) BLOOD COLLECTION TUBE WITH SURFACTANT

(75) Inventors: Bradford A. Hunsley, LaVista, NE (US); Wayne L. Ryan, Omaha, NE (US)

(73) Assignee: Streck, Inc., LaVista, NE (US)

( * ) Notice: Subject to any disclaimer, the term of this patent is extended or adjusted under 35 U.S.C. 154(b) by 0 days.

(21) Appl. No.: 12/136,374

(22) Filed: Jun. 10, 2008

(65) Prior Publication Data

US 2008/0286748 A1  Nov. 20, 2008

Related U.S. Application Data

(63) Continuation of application No. 11/369,928, filed on Mar. 7, 2006, now Pat. No. 7,419,832.

(60) Provisional application No. 60/660,284, filed on Mar. 10, 2005.

(51) Int. Cl.
G01N 33/86 (2006.01)
B01L 3/14 (2006.01)

(52) U.S. Cl. .............. 436/70; 436/63; 422/61; 422/99; 422/102; 435/2; 435/288.1; 220/23.91; 220/560.03

(58) Field of Classification Search .......... 436/63, 436/70; 422/61, 99, 102; 220/560.03, 23.91; 435/2, 288.1

See application file for complete search history.

(56) References Cited

U.S. PATENT DOCUMENTS

| 3,230,121 A | 1/1966 | Nitzsche et al. |
| 4,801,428 A | 1/1989 | Homolko et al. |
| 4,830,217 A | 5/1989 | Dufresne et al. |
| 4,852,584 A | 8/1989 | Shelby |
| 5,000,804 A | 3/1991 | Nugent |
| 5,019,243 A | 5/1991 | McEwen et al. |
| 5,173,266 A | 12/1992 | Kenney |
| 5,745,227 A | 4/1998 | Dufresne et al. |
| 5,779,938 A | 7/1998 | Naraghi et al. |
| 5,900,091 A | 5/1999 | Kenney |
| 5,914,272 A | 6/1999 | Dufresne |

(Continued)

FOREIGN PATENT DOCUMENTS

EP 0571116 A 11/1993

(Continued)

OTHER PUBLICATIONS (PADTA519) European Search Report For Application No. EP06075513 (Search Date Complete Mar. 20, 2008).

(Continued)

Primary Examiner—Maureen M Wallenhorst
(74) Attorney, Agent, or Firm—Dobrusin & Thennisch PC

(57) ABSTRACT

Improvements in blood collection and testing. In one aspect, an improved method of manufacturing a blood collection tube, particularly illustrated for use in sedimentation rate testing, including providing an elongated glass tube with an open first end for receiving a venipuncture blood sample of at least 1 ml, formed with a closed end opposite the first end; and applying to a substantial portion of the receptacle a containment barrier. The improvements also pertain to resulting blood collection tubes, additives for blood collection tubes that permit reliable sedimentation test data after 8 hours from the blood draw, and methods of administering health care using the aforenoted tubes, additives or both.

9 Claims, 1 Drawing Sheet

U.S. PATENT DOCUMENTS

| | | | |
|---|---|---|---|
| 5,984,087 | A | 11/1999 | Hacikyan |
| 6,235,239 | B1 | 5/2001 | Sharma |
| 6,514,766 | B2 | 2/2003 | Spillert et al. |
| 6,531,321 | B1 | 3/2003 | Ryan et al. |
| 6,534,016 | B1 | 3/2003 | Cohen et al. |
| 6,602,718 | B1 | 8/2003 | Augello et al. |
| 6,617,170 | B2 | 9/2003 | Augello et al. |
| 6,821,789 | B2 | 11/2004 | Augello et al. |
| 6,884,459 | B2 | 4/2005 | Caballero et al. |
| 6,910,597 | B2 | 6/2005 | Iskra |
| 6,974,701 | B2 | 12/2005 | Bouboulis |
| 7,419,832 | B2 * | 9/2008 | Hunsley et al. ............. 436/70 |
| 7,608,457 | B2 * | 10/2009 | Hunsley ................. 436/70 |
| 2002/0146677 | A1 | 10/2002 | Augello et al. |
| 2004/0137417 | A1 | 7/2004 | Ryan |
| 2006/0233676 | A1 | 10/2006 | Stein |
| 2006/0239866 | A1 | 10/2006 | Kenney |

FOREIGN PATENT DOCUMENTS

| | | | |
|---|---|---|---|
| EP | 1413874 | A | 4/2004 |
| EP | 1422509 | A | 5/2004 |

OTHER PUBLICATIONS

Westergren, Alf, "Die Senkungreaktion," Ergegn. Inn. Med. Kinderheilk, 26:577 (1924).

NCCLS, "Procedure for Determining Packed Cell Volume by the Microhematocrit Method; Approved Standard-Third Edition," H7-A3, vol. 20, No. 18 (replaces H7-A2, vol. 13 No. 9) (2000).

NCCLS, Tubes and Additives for Venous Blood Specimen Collection; Approved Standard—Fifth Edition, H1-A5, vol. 23, No. 33 (Replaces H1-A4, vol. 16, No. 13)(Dec. 2003).

NCCLS, "Reference and Selected Procedure for the Erythrocyte Sedimentation Rate (ESR) Test; Approved Standard-Fourth Edition", H2-A4, vol. 20, No. 27 (Replaces H2-A3, vol. 13, No. 8) (Dec. 2000).

ISO, "Single-Use Containers for Venous Blood Specimen Collection", ISO 6710, First edition, Aug. 1, 1995.

Drummond Scientific Company New Product Release entitled Drummond Hemato-Clad Hematocrit Tubes Meet Government Safety Recommendations, dated Feb. 28, 2005 (1 page).

FDA Advisory entitled Glass Capillary Tubes: Joint Safety Advisory About Potential Risks dated Feb. 1999 (3 pages).

Drummond Scientific Company product information Hematoclad Tubes; Plasticrit Plastic Hematocrit Tubes and Precalibrated Tubes dated Feb. 28, 2005 (4 pages).

Seditainer Evacuated Blood Collection Tube for Erythrocyte Sedimentation Rate Determination, Becton Dickinson Vacutainer Systems Europe, dated Jul. 1996 (2 pages).

Ryan, Wayne; Warrino, Dominic; Reprinted with permission Stabilizing WBCs and Immunological Markers for Flow Cytometry, Clinical Lab Products, Jan. 2005, vol. 34, No. 1, p. 31 (2 pages).

Product Literature ESR-Auto Plus, Streck, 1 page.

Product Literature ESR-100, Streck, 1 page.

Product Literature Instruments/ESR-Vacuum Tubes (7 pages).

Product Literature Instruments/Dispette 2 Kit (3 pages).

Product Literature Products/Immunology/Flow Cytometry (11 pages).

* cited by examiner

BLOOD COLLECTION TUBE WITH SURFACTANT

CLAIM OF BENEFIT OF FILING DATE

This application is a continuation of application Ser. No. 11/369,928 filed on Mar. 7, 2006, now U.S. Pat. No. 7,419,832 issued on Sep. 2, 2008, which claims the benefit of provisional application No. 60/660,284 filed Mar. 10, 2005, the contents of both of which are incorporated by reference into the present application.

FIELD OF THE INVENTION

This invention relates to the collection, transport and analysis of blood, and more particularly to a tube system for handling blood for analysis of erythrocyte sedimentation rate (ESR).

BACKGROUND OF THE INVENTION

The ESR test measures the sedimentation rate of aggregated erythrocytes in plasma. The rate of sedimentation is an indirect means of analyzing Rouleaux formation and aggregation of erythrocytes (red blood cells). Sedimentation rates tend to be an indicator of the presence, severity or both of some pathological conditions, such as those associated with certain disease states. Thus, the ESR test has been utilized as an indirect measure of these pathological conditions. Further, because of the simplicity of the test and materials for performing it, the ESR test has enjoyed common usage in laboratories, including popularity not only at large-scale regional clinical laboratories (e.g., serving a number of different health care facilities), within hospitals or research institutions, and even at local health care facilities (e.g., physician offices and clinics).

The history of ESR testing is relatively modern. Westergren developed the technique of performing an ESR determination as described in Alf Westergren, "Die senkungscreaktion", Ergegn. Inn. Med. Kinderheilk., 26:577 (1924). In the Westergren method, a venipuncture blood sample mixed with an anticoagulant (e.g., including a citrate) is placed a tube. The tube is held vertically (e.g., in a rack) at room temperature, taking precautions to avoid direct sunlight, vibrations and drafts. After a time period (typically 1 hr), the distance (x) from the bottom of the resulting plasma meniscus to the top of the column of sedimenting red cells is read and the ESR value is derived (e.g., 'ESR (Westergren 1 hr)=x mm'). The Westergren method typically employs as its measuring tube a straight tube about 30 cm long and 2.5 mm in internal diameter, thus requiring about 1 mL of blood. A citrate diluent is commonly employed as well.

Other ESR techniques are also known, such as the modified Westergren method. The Wintrobe method resembles the Westergren method, but tends to employ a shorter measuring tube (12 cm long) and omits citrate diluent from the tested blood. Historically, the Westergren and Wintrobe techniques have been manually performed. However, the techniques are now employed by semi-automated and automated instruments as well. In most of those instances, sophisticated optical detectors are employed.

As can be seen, the reliability and consistency of ESR testing can be affected by any of a number of factors, not the least of which is the nature of the tube used for containing the blood sample. For example, delays in testing or potential exposure to contaminants that deleteriously alter the surface free energy of cells are possible sources of error. It also has been recognized that variations of the nature of the measurement tube will affect test results. Specifically, it has been acknowledged that, even though plastics can be employed in certain procedures, the plastics are susceptible to (for example) plugging or plasticizer interaction with blood that are a potential for erroneous results; thus, standards prefer that blood be contained within a glass tube. See, e.g., CLSI Standard No. H2-A4, hereby expressly incorporated by reference.

Unfortunately, despite the efficacy of glass and its preference as a preferred material, many laboratory practitioners prefer the use of plastic, because of the lower risk of potential breakage and transmission of blood-borne infection.

The medical community would benefit substantially if the advantages of a glass container could be secured in a test blood tube that is also more resistant to fracture than traditional glass tubes, is capable of containing fragments if a fracture occurs, is capable of containing blood if a fracture occurs, or any combination thereof.

The use of a wrapped capillary tube for hematocrit measurement (namely the packed cell volume measurement of erythrocytes) of samples obtained from finger-stick blood draws has been proposed in U.S. Pat. Nos. 5,900,091 and 5,173,266 both expressly incorporated by reference for all purposes. In those patents a sheet of polyester film with an adhesive layer is wrapped over a small volume, thin diameter capillary tube (illustrated as having a volume of not more than 2 ml and an outside diameter of about 0.060 inches). A clay plug helps contain blood within the capillary tube. The employment of tubes of this diameter has been criticized in Clinical and Laboratory Standards Institute ("CLSI"; formerly NCCLS) Standard H2-A4, where it was also acknowledged that "[m]any so-called Westergren pipets, both glass and plastic, have an internal diameter which is less than called for in this document, i.e., less than 2.55 mm. Such pipets have been associated with spurious results, especially in specimens with a packed cell volume (PCV; "hematocrit") greater than 0.35 ("35%"). Unfortunately, pipets adequate for all blood specimens, including those with higher PCV, are not yet widely available." Accordingly, therefore, the selected procedure described by CLSI specifically calls for dilution of the specimen before measuring the sedimentation rate.

SUMMARY OF THE INVENTION

The present invention is predicated upon the discovery of improvements to blood sedimentation rate testing. In one aspect, the invention pertains to a method of manufacturing a tube for blood analysis, including the steps of providing an elongated glass tube with an open first end for receiving a blood sample of at least one ml, the tube being formed with a closed end (specifically an integral end that has a thickness of about 0.5 to 1.0 mm) opposite the first end; and applying to a substantial portion of the receptacle a containment barrier that optionally is sufficiently transparent that accurate and reproducible sedimentation rate tests are obtainable by an optical detection technique, and following a fracture of the tube, blood is contained within the tube. The present invention also contemplates a kit for blood sedimentation rate testing that includes a glass tube formed with a closed end and having an applied containment barrier thereon. In another aspect, the present invention is directed to a method for facilitating the performance of a blood analysis upon a sample of blood more than 8 hours after the blood is drawn. The present invention also contemplates blood collection tubes, glass or plastic, with or without a containment barrier, an additive that enables performance of a blood analysis upon a sample of blood (e.g., a sedimentation rate analysis) more than 8 hours after the blood is drawn, yielding results comparable with freshly drawn blood.

DETAILED DESCRIPTION

Figure 1A:
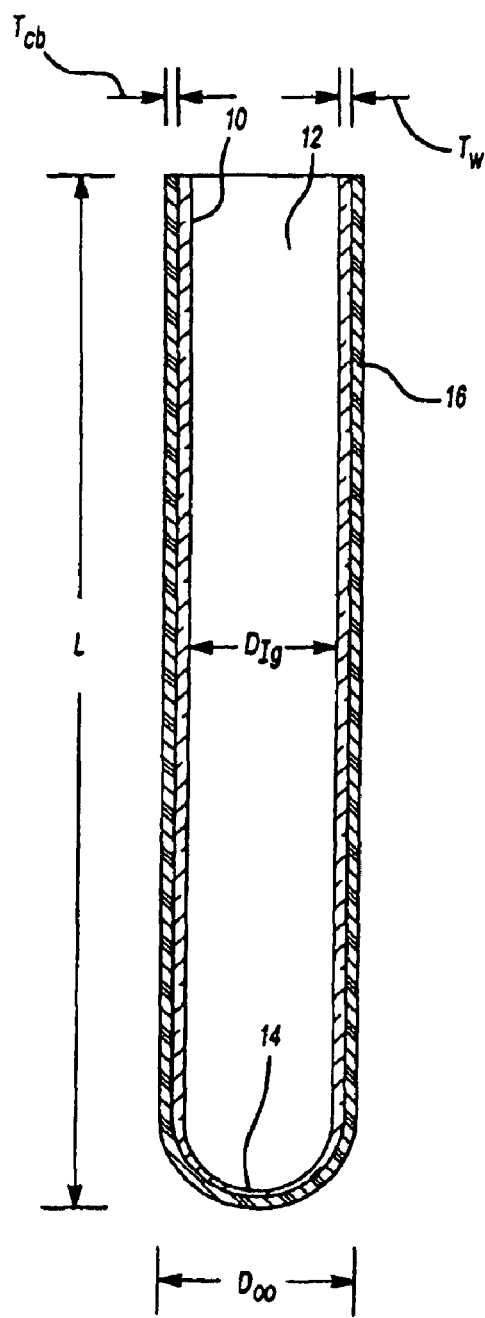
FIGS. 1A and 1B illustrate cross-sectional views of examples of tubes according to the present invention, respectively in an intact state and a broken state.

The present invention is predicated upon the discovery of improvements to blood sedimentation rate testing. In one aspect, with reference to the drawings, the invention pertains to a method of manufacturing a tube for blood sedimentation rate analysis, including the steps of providing an elongated glass tube 10 with an open first end 12 for receiving a blood sample of at least one ml, the tube being formed with a closed end 14 (specifically an integral end that has a thickness of about 0.5 to 1.0 mm) opposite the first end; and applying to a substantial portion of the receptacle a containment barrier 16 that is sufficiently transparent that accurate and reproducible sedimentation rate tests are obtainable by an optical detection technique, and following a fracture of the tube, blood is contained within the tube. In one specific embodiment, with reference to FIG. 1B, upon fracture the containment barrier maintains all fragments in substantial longitudinal alignment. The containment barrier, the glass tube or both may have one or more visual indicators, such as one or a combination of a fill-line, a label, a bar code, a transmitter for a radiofrequency identification device (RFID) or otherwise.

The tubes of the present invention may be of any suitable length and volume. One approach involves providing tubes of a volume ranging from about 1 ml to about 5 ml or larger. For example, the tubes of the present invention are particularly useful for receiving blood draws of 1.2 ml or 2.0 ml. Accordingly, methods of the present invention contemplate using tubes with ESR test equipment available commercially, such as instruments available from Streck Laboratories, Inc. under the designations ESR-100™ or ESR-Auto Plus™. Under these methods, blood samples are collected (e.g., in an evacuated glass tube as described herein). The samples are mixed with any additive contained within the tube. The sample is loaded in the test instrument (for example, without transferring to another tube), where sedimentation rate is monitored. After a pre-determined period of time, the results are outputted, e.g., in a printed form, by a visual display device, onto an electronic storage medium or any combination thereof. The results may be stored for later retrieval in a suitable electronic medium. The results may be transferred from one site to another by way of an electronic network, such as the internet.

Tubes according to the present invention will typically be substantially optically clear glass, and more specifically a USP Type III glass, such as soda lime glass. Preferably the glass will include silica as a major component, e.g., about 70% by weight or higher. Calcium oxide (e.g., from lime) and sodium oxide (e.g., from soda ash) may also be included in amounts ranging, respectively from about 7 to about 12 parts by weight, and about 12 to about 18 parts by weight, where silica is present in about 70 parts by weight. Other additives may also be included, such as oxides of calcium, magnesium, or the like. Further, the density may range from about 0.085 to about 0.095 lbs/inch. Other glasses are also possible, such as without limitation, borosilicate glasses including silica (about 70 to about 80% by weight) and boric oxide (about 7-13% by weight) with smaller amounts of the alkalis (sodium and potassium oxides) and aluminum oxide. The glass may also be a fused silica glass or another heat resistant glass that is high in silica content. It should be appreciated that certain embodiments of the present invention do not require that the tube be a glass material. It is also possible that aspects of the present invention employ art-disclosed plastic tubes.

With reference again to FIG. 1A, preferred tubes will have an overall length (L), a glass wall thickness ($T_w$), a glass inside diameter ($D_{IG}$) and an overall outside diameter ($D_{OO}$). The containment barrier 16 will also have a thickness ($T_{CB}$). The overall length will typically range from about 100 to about 300 mm (e.g., about 119 to about 121 mm). The glass wall thickness will typically range from about 0.5 to about 1.5 mm (e.g. about 0.9 to about 1.1 mm); at the closed end, the thickness might decrease relative to the side walls (e.g., to about 0.7 mm relative to about 1 mm glass wall thickness in the side walls). The glass inside diameter will range from about 4 to about 6 mm (e.g., about 4.8 to 5.4 mm). The overall outside diameter will be about 5 to about 10 mm, but more specifically will be less than about 9 mm (e.g., about 8 mm). Thus, the containment barrier thickness will typically be less than about 1 mm (e.g., about 0.5 mm). Larger or smaller dimensions are also possible.

The containment barrier is such that it covers substantially the entirety of the outer surface of the tube, although it need not, provided that the coverage is sufficient that following a fracture of the tube, blood is contained within the tube. As discussed, among the advantages derived from the present invention are the possibility that a closed-end glass tube (e.g., soda lime glass), and particularly one into which the blood sample is directly drawn, can be made to perform as well as preferred glass tubes as recommended by CLSI in Standard No. H2-A4, but they do not suffer the same potential risks associated with breakage. In one aspect, this is the result of the employment of the containment barrier, for substantially encapsulating the elongated glass tube over its entire outer surface. The containment barrier preferably includes one or more applied layers, which may include a substantially continuous layer, may include a plurality of apertures, may include a mesh, weave, a sleeve, a winding or any combination thereof, or any combination of the foregoing. Any such layers may be relatively inert relative to blood, or it may contain one or more agents for interacting with the blood upon contact therewith. For example, the containment barrier may carry an anti-microbial, an absorbent (e.g., a suitable polymer, treated fiber or other absorbent material as discussed herein), a molecular sieve, or any combination thereof.

Application of the containment barrier to the tube may be done by any of a number of different techniques including, for example, a step of spraying, dipping, brushing, vapor depositing, wrapping, laminating, shrink-wrapping, any combination thereof or some other suitable surface treatment technique. It is possible that one or more intermediate layers may be employed, such as a primer layer, an adhesive layer or any combination thereof. A particularly preferred approach is to coat an elongated, closed end glass tube with a thin layer of a plastic (e.g., by spraying, dipping or brushing) over its outer surface, its inner surface or both, for forming a containment barrier. In such instances, it is possible that a solution, emulsion or other dispersion that includes the plastic or a precursor is contacted with the glass tube for forming the containment barrier. For a shrink-fitting or shrink-wrapping approach, it may be possible to employ a sheet of material that is placed over the glass tube and then is shrunk to be intimately secured with the tube. It may also be possible to employ a preformed casing (e.g., formed in the shape of one of the separable portions of a pill capsule) that is slipped over the tube and then shrunk to be intimately joined with the tube. Such fitting may also be accomplished by selection of a material that differs in thermal expansion coefficient relative to the glass, so that one or both of the casing or the tube can be heated or cooled to accomplish a fit, and upon return to room temperature the casing material will be placed in hoop tension about the tube.

Figure 1B:
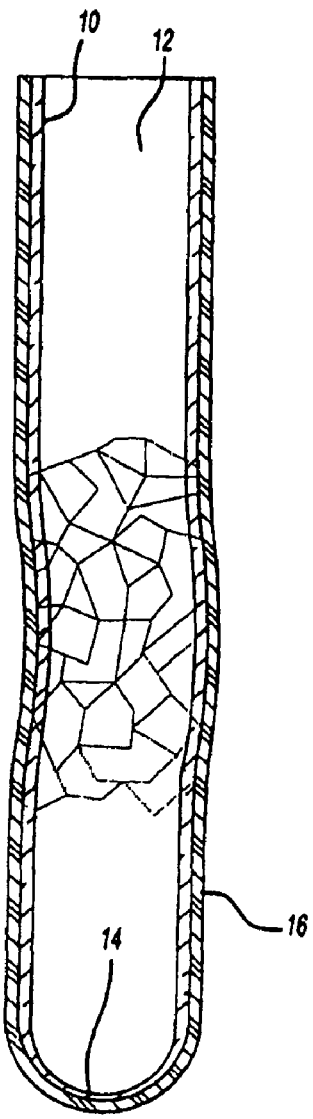

The containment barrier will typically be a material, structure or combination thereof that is sufficiently rigid that it will withstand rupture in the presence of load events sufficient to break the tube if no barrier is present. Thus, as seen in FIG. 1B, one such structure and material combination, though a load event (e.g., being dropped to a hard surface from a distance of about 1 to about 3 meters, being stepped upon by a person weighing more than about 50 kg, a collision with another body in motion, or otherwise) is sufficient to shatter the tube (e.g., the load exceeds the ultimate tensile load of the tube material), the containment barrier contains the contents of the tube, including tube fragments, and may also, upon fracture the containment barrier, maintain all fragments in substantial longitudinal alignment. Typically, the containment barrier will be one or more relatively uniform outer layers that substantially encapsulate the tube, such as that attainable by wrapping a film, or substantially uniformly applying the containment barrier layer as an at least partially hardenable liquid coating (e.g., from a solution having a polymer dissolved or dispersed therein, from a melt, or otherwise).

The material selected for the containment barrier may be any suitable material. If it is to overlie substantially the entirety of the outer surface of the tube, the material typically will be a substantially amorphous ceramic, plastic, wax or combination thereof. Examples of suitable plastics include, without limitation, polythene naphthalate, cellulose acetate, polycarbonate (e.g., LEXAN®), polyethylene, polypropylene, poly-vinyl fluoride, polyimide, polyester (e.g., Mylar®, Melinex® or the like), polyamide (e.g., Nylon 6,6), polyvinyl chloride, combinations thereof or the like. Plastics may be treated so that they have a release coat (e.g., silicone), heat stability, an adhesive applied, a color coated, a moisture absorbent applied, an image (e.g., a holographic image), or otherwise treated to locally or uniformly modify a characteristic of the material. The plastics as used in the containment barrier preferably will be substantially transparent for facilitating optical detection and monitoring of sedimentation rates. However, some crystallinity may be possibly. For example, it is possible that an axially oriented plastic is employed for helping provide enhanced mechanical properties.

The containment barrier may also be configured so that it is tamper evident (e.g., removal of the barrier reveals a visual or other detectable message or indicator), or another indicator is provided to denote it is not an unused tube. For example, a containment layer may be applied on a tube that has been evacuated, has additives already present or both, and which is sealed. The containment barrier would overly at least part of the seal, thus hindering opening of the seal. Further the tube itself may be provided with an indicator to denote that it has a containment barrier present. For example, the tube might carry one portion of a message or indicator having two or more portions, such as part of a word. The containment barrier would in turn be printed with or otherwise marked with the second part of the message. Thus when the containment barrier is present the portions of the message form a complete message.

In one embodiment, the containment barrier of the present invention further includes a tear strip, perforations or some other structure that would facilitate removal of the containment barrier so that it, the tube, the seal (e.g., a cap or possibly even the containment barrier itself) or any combination thereof could be recycled. The present methods thus contemplate a step of recycling within its scope.

The present invention also contemplates a kit for blood sedimentation rate testing that includes a glass tube formed with a closed end and having an applied containment barrier thereon. In another aspect, the present invention is directed to a method for facilitating the reliable performance of a blood sedimentation rate upon a sample of blood more than 8 hours after the blood is drawn.

In accordance with one embodiment, the present invention contemplates the manufacture of a blood collection tube for a sedimentation rate test, pursuant to which a step of transferring blood from a conventional blood collection tube into a separate tube for performing the test is avoided. Specifically, the blood collection tube serves not only as the receptacle into which blood is immediately stored upon a patient draw, but also serves to carry the blood during the sedimentation rate test. In this manner, it is possible to reduce handling steps that are a potential source of test error and exposure to blood pathogens.

Under this approach, it is therefore contemplated at least one step of evacuating the elongated glass tube to below atmospheric pressure and sealing the evacuated glass tube (e.g., with an art-disclosed cap). Such approaches to evacuation and sealing are disclosed, for example, in published U.S. Patent Application No. 20040137417 (Ryan), hereby incorporated by reference. Further, whether an evacuation step is employed or not, it is possible that the tubes will be prepared so that upon receipt thereof, a user (e.g., a medical practitioner or other technician), the tubes will contain an additive (typically in a liquid form, but which may be solid or semi-solid (e.g., a gel, cream or paste)). It will be appreciated that one advantage of the present invention is that it permits for the use of dry additives and wet additives, unlike plastic tubes which typically require dry additives, in view of the propensity for moisture loss inherent with a plastic tube.

Therefore the method may further include a step of introducing into the tube, prior to introducing any blood, an additive selected from the group consisting of a preservative, an anticoagulant, an antimicrobial, a surfactant, or any combination thereof. More particularly, the method may further include a step of introducing into the tube, prior to introducing any blood, a surfactant and an additive selected from the group consisting of a preservative, an anticoagulant, an antimicrobial, or any combination thereof. Examples of additives generally are disclosed, without limitation in Tubes according to the present invention preferably satisfy the criteria set forth in Annex E of ISO 6710: 1995(E) for "Single-use containers for venous blood specimen collection", incorporated by reference. Examples of anti-coagulant additives include, without limitation, an anticoagulant agent selected from the group consisting of ethylene diamine tetra acetic acid (EDTA), salts of EDTA, ethylene glycol tetra acetic acid (EGTA), salts of EGTA, hirudin, heparin, citric acid, salts of citric acid, oxalic acid, salts of oxalic acid (e.g., potassium oxalate, sodium oxalate, or the like), and a combination thereof. They may be present in sufficient art disclosed amounts. For example, one approach is to employ as an anti-coagulant an aqueous combination of trisodium citrate, and citric acid, monohydrate wherein the relative amount (by weight) of trisodium citrate, dehydrate to citric acid, monohydrate is about 5:1 to about 12:1, and more specifically is about 8:1.

An example of a suitable anti-microbial includes, for example, sodium azide thimerosal, chloramphenicol, bromo-5 nitro 1,3 dioxane, tetradecyltrimethylammonium bromide or the like in their art-disclosed amounts.

Additional additives may optionally be added in the tubes. Such additional and optional compounds may include, without limitation, cell permeabilizing agents for substantially gaining access to intracellular analytes/epitopes and/or for lysing red blood cells; proteins that substantially protect the cells during processing and/or substantially reduce non-specific binding of probes; serum/lipoproteins that substantially protect cells during processing and/or substantially reduce non-specific binding of probes; RNAse inhibitors which substantially inhibit digestion of RNA and/or substantially maintain RNA integrity; nucleic acid stabilizers which substantially inhibit the degradation of nucleic acids and nucleic acid containing compounds; amino acids/polypeptides which substantially enhance binding of probes/antibodies to epitopes and/or substantially increases the observable signal; fixatives which substantially preserve cell integrity especially for permeabilization agents, and may preserve some epitopes; anticoagulants which substantially decreases clotting of red blood cells, chelates calcium and/or may help maintain WBC integrity/viability; protease inhibitors which substantially decreases degradation of protein epitopes; antioxidants/reducing agents which substantially prevent hemolysis of red blood cells and/or substantially prevent oxidation of peptides, and/or substantially maintain epitopes; nucleic acid dyes that generally serve to label/identify nucleic acid; carbohydrates which substantially maintain cellular integrity and/or osmolarity; and, polyacrylic acids which substantially enhance the binding of probes and/or antibodies to epitopes; and/or substantially increases signal. One of skill in the art should be able to determine the usefulness and quantities of such optional compounds by routine testing and knowledge of the art. Within the above, particular examples of additives include, without limitation, Cell permeabilizing agents such as: DMSO (Dimethyl Sulfoxide), Ethylene glycol, Polyethylene glycol, Glycerin, Cellosolves (ethylene glycol dimethyl ether) (phenoxyethanol), Triton® X 100, Triton® X 705 (non-ionic detergents), 1-methyl-2-pyrrolidinone, Tween® 20, Tween® 40 (non-ionic), Brij® 35 (detergent), Polyoxyethylene ether (Polyox), Sodium cholate, Ethylene oxide polymers, Monensin, Monactin, Pentachlorophenol, 2,4 dinitrophenol, saponin, SDS (sodium dodecyl sulfate); Proteins such as: Biotin, Albumins (egg, bovine), Gelatin, and similar such compounds as should be known to one of skill in the art; RNAse inhibitors such as: human placenta derived RNAse inhibitor, and similar such compounds should be known to one of skill in the art; Nucleic acid stabilizers such as: Guanidinium hydrochloride, Polycations such as Polyethylenimine), and similar such compounds as should be known to one of skill in the art; Amino acids/polypeptides such as: Glutamic acid, Glycine, Aspartic acid, and similar such compounds as should be known to one of skill in the art; Fixatives such as: Aldehydes (formaldehyde and glutaraldehyde), Alcohols (ethanol, methanol), and similar such compounds as should be known to one of skill in the art; Anticoagulants such as: EDTA (Ethylene Diamine Tetra acetic acid.), and similar such compounds as should be known to one of skill in the art; ACD (Acid Citrate Dextrose), Heparin, and similar such compounds as should be known to one of skill in the art; Protease Inhibitors such as: EDTA, PMSF (phenyl methyl sulfonyl fluoride), AEBSF (2-Aminoethyl benzene sulfonyl fluoride), and similar such compounds as should be known to one of skill in the art; Antioxidants/Reducing agents such as: Trolox, a-tocopherol, B-mercaptoethanol, and similar such compounds as should be known to one of skill in the art; Nucleic Acid Dyes such as: DAPI (Diamidino 2-phenylindole), Propidium Iodide, Fluorescein diacetate, and similar such compounds as should be known to one of skill in the art; Carbohydrates such as: Sugars (sucrose), cellulose, and similar such compounds as should be known to one of skill in the art. It should be appreciated that the above specific listings of compounds may contain a measure of overlap, which recognizes the sometimes-overlapping function of certain specific compounds. One of skill in the art should understand and appreciate this aspect of the disclosure.

In another aspect of the present invention, methods of using the tubes and kits of the present invention contemplate the stabilization of one or more of the components of a blood sample so that sedimentation rate testing, though it may occur substantially contemporaneously with the blood draw, alternatively or additionally may occur (in a consistent and reproducible manner that approximates that of a fresh blood sample) after a delay of more than about 12 hours, and more specifically more than about 24 hours (e.g., after a period of 36, 48, 60, 72 hours or more have elapsed). One embodiment contemplates a period of at least 4 days between the time of the blood draw and sedimentation rate testing. In this manner, it is possible to offer sedimentation rate test blood draw services to remotely located populations, where sedimentation rate test equipment may be unavailable, and thereafter to transport the drawn blood to a remote location for subsequent analysis (whether contained in the tube or removed from the tube during or for analysis), without compromising the blood sample.

With reference to the above step of transporting the blood, and as for any other handling steps that may occur prior to testing, the present invention also contemplates that the blood sample may be kept at ambient temperature (e.g., about room temperature), raised or lowered relative to ambient, or any combination thereof. For example, a portable heater or refrigeration device (e.g., a solid state thermoelectric device) may be used for storing blood. One specific approach contemplates maintaining the temperature of the sample below about 20° C., and more specifically below about 15° C. (e.g., about 2 to about 10° C.).

Without intending to be bound by theory, it is believed that the employment of a particular additive selection in the tube contributes to stabilization of the sample so that substantial delays (e.g., for a period of at least about two hours longer than what would be obtainable for a fresh whole blood without the particular additive selection) may take place between the time of the blood draw and the time of sedimentation rate testing. In particular, it is believed that the employment of a surfactant in the additive selection helps contribute to this advantage. Though other surfactants are possible, including cationic, anionic, Zwitterionic or any combination thereof, a specific example of a class of surfactants for the present invention is nonionic surfactants.

More particularly, the nonionic surfactants of the present invention are selected to have an average monomer molecular weight in the range of about 500 to about 2000, and more specifically about 800 to about 1600, and still more specifically about 1100 to about 1400 (e.g., about 1200). Further, the surfactant will have an aggregation number that ranges from about 20 to about 120 (e.g., about 40). The surfactant typically will be of substantially homogeneous purity. The surfactant preferably is free of clouding under the conditions to which it will be exposed prior to and during sedimentation rate testing.

A preferred group of surfactants typically include a hydrophobic moiety (e.g., an alkyl chain) in combination with a hydrophilic moiety (e.g., a polyoxyethylene chain), and further may include an ether linkage, for example a surfactant based upon polyoxyethylene alkyl ether. In one embodiment, the nonionic surfactant is one of the form $C_xE_y$, where x is the number of carbons in the alkyl chain (C) and y is the number of ethylene oxide units in the polyoxyethylene chain (E). In this respect specific examples will employ an x value ranging from about 6 to about 18 (e.g., about 12) and a y value ranging from about 4 to about 40 (e.g., about 23).

Thus, it is possible that the surfactants are based upon polyoxyethylene alcohols, polyoxyethylene alkylphenols, or a combination thereof, and particularly surfactants of such type having one or more ether linkages. Examples of specific surfactant ingredients include, without limitation, polyoxyethylene (20) sorbitan monolaurate, polyoxyethylene (23) lauryl ether, polyoxyethylene (9) mono(octylphenyl)ether, polyoxyethylene octylphenyl ether, or any combination thereof. Specific commercial examples include, without limitation, Tween® 20, Tween® 40, Tween®80, Brij® 30, Brij® 35, Brij® 58, Triton® X-100, Triton® X-114, Triton® X-705, or any combination thereof.

Of course, it may be possible to employ any of a number of other surfactants, such as the organosilicone surfactant (namely polyalkyleneoxide modified polydimethylsiloxane) disclosed in U.S. Pat. Nos. 5,914,272 and 5,779,983 (hereby incorporated by reference), alcohols, esters of fatty acids, mercaptans, and alkylamines; nonionic surfactants containing an amide group; polyol ester surfactants or any combination thereof.

The amount of the surfactant that is employed is preferably such that if the surfactant clouds, then the amount of clouding will not impair the ability to monitor the sedimentation rate. It is also used in sufficient amount that it is capable of providing reproducible sedimentation rate tests (in a consistent and reproducible manner that approximates that of a fresh blood sample) after a delay of more than about 12 hours, and more specifically more than about 24 hours (e.g., after a period of 36, 48, 60, 72 hours or more have elapsed), and optionally when the blood sample is maintained at ambient temperature (though it may be refrigerated or heated as described herein). One embodiment contemplates usage of the surfactant in an amount that a sedimentation rate test approximating that of fresh blood is obtained after a period of at least 4 days between the time of the blood draw and sedimentation rate testing. Examples of concentrations typically will range from about 0.1 g/l to about 5 g/l, more specifically about 0.5 g/l to about 3 g/l, and still more specifically about 0.9 to about 1.5 g/l (e.g., about 1.0 g/l). In another approach, the concentration of the surfactant is less than about 10% of the concentration of the anti-coagulant, and more specifically is less than about 5% of the concentration of the anti-coagulant.

The total amount of additive in the tube will vary as desired. However, for blood draws of about 1 to 2 ml, it is preferred that the amount not exceed about 25 to about 60% of the total resulting volume (namely, additive plus blood sample). For example, with a tube drawing having about 1.2 ml of blood, about 0.34 ml of additive will be present. For a tube drawing having about 2.0 ml of blood, about 0.56 ml of additive will be present.

The tubes of the present invention may be included in a kit adapted for collection, transport, or analysis of the drawn blood sample. Examples of components that might be part of such a kit include, without limitation an alcohol swab, gauze, a tube holder, a tube rack, a tourniquet, a glove, another cell collection tube (with or without conventional cell analysis additives inside such tube), needle (with hub, part of a syringe assembly including barrel and plunger, or with wings connected via a hub and tubing to another needle for delivery to the device 100 or other collection tubes), lancet, adhesive strip, syringe, test strip (allowing the blood to flow directly onto a glass or plastic strip containing reagents for cell analysis), glass or plastic strip containing reagents for cell analysis (e.g., immunoassay), packaging (e.g., plastic bag, compartmentalized plastic enclosure, and the like) to store the desired components, packaging to transport the blood sample stored in the tube after collection, a timer, a worksheet (e.g., for recording sedimentation levels at different times), or any combination thereof. It is preferred that any components that may come in physical contact with the blood sample be sterilized and that the packaging is constructed to substantially maintain this sterile environment.

The packaging may also include a suitable moisture absorbent for absorbing blood in the event of spillage, such as a mass of absorbent material that is contained within at least a partially moisture permeable covering. The absorbent material may include a cellulosic material, (e.g., cotton, wood pulp, or the like) that is optionally modified or cross-linked. Synthetic materials may also be used, such as art-disclosed super-absorbent polymers or gels, plastic (e.g., polyolefin or polyester) fibers, absorbent foams. The absorbent material may also be of a suitable structure for enhancing absorption characteristics, such as capillary channel structures, structures with large surface areas for enhancing absorption, surface treated structures or any combination thereof. Any combinations of the foregoing materials may also be used, such as a super-absorbent polymer, combined with a wood pulp including co-formed fibrous structures.

The present invention also contemplates methods of administering health care diagnosis or treatment to remote populations. For example, one such method contemplates coordinating the delivery of a cell (e.g., a blood cell) sampling kit to at least one remote location, where a blood sample is drawn from a plurality of persons and is analyzed more than 12 (and more specifically more than 24 hours, and even up to at least 4 days after each sample is drawn. Information is received about results of an analysis (e.g., an ESR or ZSR analysis) of the patient sample. Administration of a pharmacological therapy (which optionally may include a generic drug) to a plurality of such persons whose sample indicates treatment is necessary is then performed. Any or all of the steps of coordinating delivery, receiving information and administration of therapy can all be performed from a site that is remote from the site of the patient blood draw. Another aspect of these methods contemplates coordinating the transport of the sample from the blood draw site to the site where it is analyzed. The transport may take place in ambient conditions or the sample may be heated or refrigerated, such as by containing it within a portable solid state thermoelectric device. The present invention therefore provides advantages over conventional health care methods, by enabling reliable blood testing to be obtained in regions where health care workers may not otherwise have access to appropriate instrumentation, but need to rely upon a remote analysis for diagnosis. The invention thus can be employed in diagnosing, treating or monitoring not only traditional conditions for which sedimentation rate testing has been done (e.g., acute and chronic inflammation, infections, cancers, and various autoimmune diseases), but in connection with other tests as described herein (e.g., blood draws for flow cytometry or other hematological analysis, such as might be used to diagnose, treat or monitor cancer, HIV or some other condition).

Aspects of the present invention are not limited to sedimentation rate testing. For example, it is possible that conventional closed ended blood collection tubes may be adapted to have a containment barrier. In this regard, other additives may be included as well, such as a fixative selected from the group consisting of: diazolidinyl urea, imidazolidinyl urea, dimethoylol-5,5dimethylhydantoin, dimethylol urea, 2-bromo-2.-nitropropane-1,3-diol, oxazolidines, sodium hydroxymethyl glycinate, 5-hydroxymethoxymethyl-1-1aza-3,7-dioxabicyclo [3.3.0]octane, 5-hydroxymethyl-1-1aza-3,7dioxabicyclo [3.3.0]octane, 5-hydroxypoly[methyleneoxy]methyl-1-1 aza-3, 7dioxabi cyclo [3.3.0]octane, quaternary adamantine and combinations thereof. In this regard, the blood may be analyzed by one or more other automated hematology analyzers, such as a flow cytometer. Further it is possible that the same blood sample that undergoes a sedimentation rate test may then be diluted and analyzed for at least one other test by an automated instrument.

The following examples further illustrate aspects of the present invention.

EXAMPLE 1

A blood sample is drawn by venipuncture from a patient and is captured immediately upon drawing by a previously evacuated soda lime glass tube to which a layer of MYLAR® film is coated over its exterior. The glass tube contains the ingredients of TABLE 1. After refrigeration for 12 hours at a temperature varying between 2 and 10° C., the sample is repeatedly tested by the Westergren method at intervals of two hours for the following two days. Consistent results are observed over the period of 12 to 72 hours from blood draw.

| ADDITIVE COMPOSITION | | | |
|---|---|---|---|
| | per liter | % w/v | |
| Trisodium Citrate, dihydrate | 32 g | 3.2 | Anti-coagulant |
| Citric Acid, monohydrate | 4.2 g | 0.42 | Anti-coagulant |
| Sodium Azide | 0.50 g | 0.05 | Anti-microbial |
| Brij ® 35 | 1.0 g | 0.10 | Surfactant |

EXAMPLE 2

Example 1 is repeated, except the glass tube has no barrier layer. The blood tested shows the same sedimentation rate as the glass tube with the barrier layer. However, upon dropping to the ground the glass fractures and blood spills.

EXAMPLE 3

Examples 1 and 2 are repeated, except that the surfactant is excluded from the additives. Testing performed at two hour intervals show that after about 6 hours, inconsistent results are thereafter obtained, with a gradual and substantially continuous change of sedimentation rate during the period following 12 to 72 hours from blood draw.

Blood drawn and handled in accordance with the present invention may be analyzed by any of a number of different techniques, such as are disclosed in CLSI Standard No. H2-A4, hereby expressly incorporated by reference, including without limitation, the Westergren method of erythrocyte sedimentation rate testing, modified Westergren method of erythrocyte sedimentation rate testing, the Wintrobe method of erythrocyte sedimentation rate testing, Zeta Sedimentation Ratio Determination (ZSR) using centrifugation, or otherwise. The tests may be performed manually, or using a semi-automated or automated instrument.

The methods herein contemplate steps of using tubes according to the present invention in a clinical laboratory for diagnosis of a condition, for monitoring a response of a patient to therapy, for monitoring quality and operation of a measurement instrument or system, for calibrating a measurement instrument or system, or any combination thereof.

Tubes according to the present invention preferably satisfy the criteria set forth in ISO 6710: 1995(E) for "Single-use containers for venous blood specimen collection". Accordingly, users of the present invention include, without limitation, clinical laboratory personnel, manufacturers of instruments or systems, distributors of instruments or systems, manufacturers of tubes, distributors of tubes, or otherwise.

It will be further appreciated that functions or structures of a plurality of components or steps may be combined into a single component or step, or the functions or structures of one step or component may be split among plural steps or components. For example, the containment barrier might be divided into plural components for performing the functions described. Alternatively, functions performed by one of the components might be split among or performed by other components (e.g., a tempering or other heat treating process may be employed with glass so that upon fracture, the fracture occurs in a predetermined manner). The present invention contemplates all of these combinations. Unless stated otherwise, concentrations, amounts, dimensions and geometries of the various structures depicted herein are not intended to be restrictive of the invention, and others are possible. References to "blood" herein generally pertain to human blood. However, the present invention is not intended to be limited only to human blood. Blood of other mammals and other animals may also be handled or otherwise processed using the present invention. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The invention claimed is:

1. A kit for performing a blood sedimentation rate analysis, comprising:
  a) a substantially optically clear glass tube having an overall length of about 100 to about 300 mm and a wall thickness of about 0.5 to about 1.5 mm, and having a plastic containment barrier that covers substantially the entirety of the outer surface of the tube with a thickness of less than about 1 mm and a closed end, and containing an additive including a polyoxyethylene lauryl ether surfactant that is free of clouding under the conditions to which it will be exposed prior to and during sedimentation rate testing and at least one additional additive selected from the group consisting of an anti-microbial, an anti-coagulant, a preservative, or any combination thereof, wherein the surfactant is present in the tube in sufficient amount that it is capable of providing reproducible sedimentation rate tests in a consistent and reproducible manner that approximates that of a fresh blood sample after a delay of more than about 6 hours; and b) at least two components for performing a blood sedimentation rate analysis selected from the group consisting of an alcohol swab, gauze, a tube holder, a tube rack for performing a blood sedimentation rate analysis, a tourniquet, a glove, another cell collection tube, needle, lancet, adhesive strip, syringe, test strip, glass or plastic strip containing reagents for cell analysis, packaging to store any desired components, packaging to transport a blood sample stored in the tube after collection, a timer, a worksheet, or any combination thereof.

2. A blood collection tube for sedimentation rate analysis, comprising:

an evacuated elongated glass tube with an open first end for receiving a venipuncture blood sample of at least 1 ml, formed with a closed end opposite the first end;

a plastic containment barrier that is substantially transparent and substantially encapsulates the exterior surface of the elongated glass tube so that following a fracture of the tube, blood is contained within the tube;

and a polyoxyethylene lauryl ether surfactant, being present within the tube in sufficient amount that it is capable of providing a reproducible sedimentation rate test in a consistent and reproducible manner that approximates that of a fresh blood sample after a delay of more than about 6 hours, and that is free of clouding under the conditions to which it will be exposed prior to and during sedimentation rate testing.

3. The blood collection tube of claim 2, wherein the surfactant is present in a concentration of about 0.1 g/l to about 5 g/l, the surfactant is selected to have an average monomer molecular weight in the range of about 500 to about 2000, and the surfactant will have an aggregation number that ranges from about 20 to about 120; and further comprising at least one additional additive placed within the tube selected from the group consisting of an anti-microbial, an anti-coagulant, a preservative, or any combination thereof.

4. The blood collection tube of claim 3, wherein the surfactant is present such that a sedimentation rate test approximating that of fresh blood is obtained after a period of at least 4 days between the time of a blood draw and sedimentation rate testing.

5. A method for performing an erythrocyte sedimentation rate analysis, comprising:

drawing a venipuncture blood sample into an evacuated elongated glass tube with an open first end and a closed end opposite the first end, the elongated glass tube including a plastic containment barrier that is substantially transparent and substantially encapsulates the exterior surface of the elongated glass tube so that following a fracture of the tube, the blood sample is contained within the tube;

contacting the blood sample with a polyoxyethylene lauryl ether surfactant in the glass tube, the surfactant being free of clouding under the conditions to which it will be exposed prior to and during sedimentation rate testing and being present within the tube in a sufficient amount that it is capable of providing a reproducible sedimentation rate test in a consistent and reproducible manner that approximates that of a fresh blood sample after a delay of more than about 6 hours; and performing the erythrocyte sedimentation rate analysis while the blood sample is contained within the tube.

6. The method of claim 5, wherein the surfactant is a nonionic surfactant of the form $C_xE_y$, where C is an alkyl chain and E is a polyoxyethylene chain and where x is the number of carbons in the alkyl chain and y is the number of ethylene oxide units in the polyoxyethylene chain.

7. The method of claim 6, wherein x is from about 6 to about 18 and y is from about 4 to about 40.

8. The method of claim 7, wherein the surfactant is present in a concentration of about 0.1 g/l to about 5 g/l, the surfactant is selected to have an average monomer molecular weight in the range of about 500 to about 2000, and the surfactant will have an aggregation number that ranges from about 20 to about 120.

9. The method of claim 6, further comprising contacting the blood sample in the tube with at least one additional additive placed in the tube selected from the group consisting of an anti-microbial, an anti-coagulant, a preservative, or any combination thereof.

* * * * *